United States Patent [19]
Knap et al.

[11] Patent Number: 5,885,618
[45] Date of Patent: Mar. 23, 1999

[54] COMPRESSIBLE ENZYME POWDER

[75] Inventors: Inge Helmer Knap, Farum; Breian Knudsen, Albertslund, both of Denmark

[73] Assignee: Novo Nordisk A/S, Bagsvaerd, Denmark

[21] Appl. No.: 553,277

[22] PCT Filed: Jun. 16, 1994

[86] PCT No.: PCT/DK94/00237
§ 371 Date: Nov. 28, 1995
§ 102(e) Date: Nov. 28, 1995

[87] PCT Pub. No.: WO95/00121
PCT Pub. Date: Jan. 5, 1995

[30] Foreign Application Priority Data

Jun. 18, 1993 [DK] Denmark .................. 0719/93

[51] Int. Cl.$^6$ .................. A61K 9/20; A61K 38/54
[52] U.S. Cl. .................. 424/499; 424/489; 424/94.2
[58] Field of Search .................. 424/94.1, 94.2, 424/493, 499, 489; 426/56; 435/183, 187, 188

[56] References Cited

U.S. PATENT DOCUMENTS

| | | | |
|---|---|---|---|
| 3,721,725 | 3/1973 | Briggs et al. | 264/6 |
| 3,928,566 | 12/1975 | Briggs et al. | 424/94 |
| 3,932,943 | 1/1976 | Briggs et al. | 34/5 |
| 4,551,177 | 11/1985 | Trubiano et al. | 106/210 |

OTHER PUBLICATIONS

Johnson, K., "Beano–Reducing the Flatulence Factor", East West Natural Health, vol. 22, No. 1, p. 143(3), Feb. 1992.

Abstract JP 4008288, Jan. 13, 1992.

Abstract DE 2140747, Aug. 13, 1971.

Abstract SU 1024087, Jun. 23, 1983.

JP 62–269685, Nov. 24, 1987.

*Primary Examiner*—Michael P. Woodward
*Assistant Examiner*—Brenda G. Brumback
*Attorney, Agent, or Firm*—Steve T. Zelson, Esq.; Cheryl H. Agris, Esq.

[57] ABSTRACT

This invention relates to a directly compressible enzyme powder produced by mixing a liquid enzyme preparation with a suitable carrier, using the principle of wet granulation, whereby the step of freeze drying and spray-drying is avoided. The resulting enzyme powder has extraordinary good compression qualities and may directly be tabletted.

60 Claims, No Drawings

# COMPRESSIBLE ENZYME POWDER

This application claims priority of DK 0719/93 filed 18 Jun., 1993 under 35 U.S.C. 119 and priority of PCT/DK94/00237 under 35 U.S.C. 120.

FIELD OF INVENTION

This invention relates to a directly compressible enzyme powder useful for producing enzyme-containing tablets. It also relates to a process for the preparation of such a powder and to a tablet prepared from such a powder.

BACKGROUND OF THE INVENTION

In the art of tablet technology tablets are often made from a spray-dried powder containing an active component which after spray-drying and prior to tabletting is mixed with one or more components (for example flow-aids) needed for tabletting to take place. Flow-aids are added in order to make the powder for tabletting free-flowing. Free-flowing means that the powder may be poured through a hopper without caking or sticking to the side walls. An example of a typical flow-aid is fumed silicon dioxide.

By using this traditional method the spray-dried powder is normally very dusty and difficult to handle, so there are safety problems by handling them if the active component has an allergy potential. Often this very dusty powder also has to be handled in more than one operation: First the spray-dried powder is mixed with flow-aids as described above, and then a granulation may be needed in order to give the powder the right strength for tabletting.

To overcome these difficulties much effort has been put into developing directly compressible powders which are non-dusting and free-flowing, for instance by spray-drying an emulsion containing a vitamin, a carbohydrate and a gelatin (see U.S. Pat. No. 4,892,889).

Tablets containing enzymes such as amylases, proteases, lipases, invertases, papain, trypsin, pepsin, pancreatin, etc. have been described long ago (see for instance U.S. Pat. No. 3,515,642). They are made by the conventional methods of converting a freeze-dried or spray-dried powder into tablets.

SUMMARY OF THE INVENTION

In accordance with this invention, it has surprisingly been found that a directly compressible enzyme powder may be produced by mixing a liquid enzyme preparation with a suitable carrier, using the principle of wet granulation, whereby the step of freeze-drying and spray-drying is avoided. The resulting enzyme powder has extraordinary good compression qualities and may directly be tabletted.

Accordingly, in a first aspect the present invention relates to a directly compressible powder, which comprises a carbohydrate and an enzyme. In a second aspect the invention relates to a process for the preparation of such a powder and to a tablet prepared from such a powder.

DETAILED DISCLOSURE OF THE INVENTION

Directly Compressible Powders

According to this invention the directly compressible powder comprises a carrier of carbohydrate(s) and one or more enzymes.

In the present context a directly compressible powder is a powder which may be directly tabletted without adding any excipients except possibly a lubricant. This means that no flow-aids and binders are added before tabletting, but a lubricant such as stearic acid, hydrogenated vegetable oil or Mg stearate may be added, if necessary.

In order to make the powder directly compressible the demands made on the carrier are quite large: It has to be a material with plastic properties (so that the resulting tablet does not fall apart before use), on the other hand, when the tablet is used the carrier must be able to absorb liquid and make the tablet disintegrate. Moreover, as the powder is directly compressible, the powder should be free-flowing, which means that no flow-aids need to be added before tabletting. Lastly, as the resulting tablet may be ingested by humans, the carrier should preferably be non-toxic.

In order to make the powder directly compressible the water content of the powder may be of at the most 10% (w/w), preferably in the range of 3–5% (w/w), and the particles of the powder may be in the range from 50 to 1500 $\mu$m, preferably in the range from 125 to 1000 $\mu$m, more preferably in the range from 150 to 700 $\mu$m.

Some carbohydrates or mixtures of carbohydrates posses the above mentioned properties of workable carriers. It has especially been found that starch, sugar and sugar alcohols or any mixtures thereof may give very good carriers. For instance, the starch may be maize starch, potato starch, rice starch, wheat starch, in fact any starch of vegetable origin. The sugar may be any mono-, di- or oligosaccharide, e.g. sucrose, maltose, lactose, galactose, fructose or glucose. The sugar alcohol may be any alcohol of a mono-, di- or trisac-charide, e.g. sorbitol, mannitol or xylitol. All these carbohydrates are available from normal commercial sources.

It has been found that a superior carrier consists of a mixture of maize starch and sorbitol. The maize starch is preferably present in an amount of 65–90% (w/w), while the sorbitol is preferably present in an amount of 10–35% (w/w), more preferably the maize starch is present in an amount of 75% (w/w) and the sorbitol in an amount of 25 k(w/w).

Enzymes

According to the invention, the enzyme could be any enzyme, e.g. one which may be used in the preparation of food and feed, a medicinal enzyme, an enzyme used for digestive aids, an enzyme useful for technical applications or any application where a precise and safe dosage of an enzyme is needed or desirable. The enzyme may be chosen from oxidoreductases such as peroxidases and glucoseoxidases, hydrolases such as carbohydrases (e.g. amylases, hemicellulases, cellulases, inulinases, lactases and galactosidases), proteases (e.g. serin proteases and aspartic proteases), lipases and phytases, isomerases such as glucoseisomerases or any mixture thereof. The enzyme may be of microbial, plant or animal origin. The enzyme may be a recombinant enzyme or an enzyme recovered from its natural source.

The enzyme is added to the carrier as a liquid enzyme preparation. The liquid enzyme preparation may be an enzyme concentrate. An enzyme concentrate is produced by removing the production strain from the fermentation broth, for example by filtration or centrifugation, whereafter the liquid is concentrated to the desired enzyme strength, for example by ultrafiltration or by evaporation. The enzyme concentrate may be stabilized by preservatives such as sorbate or benzoate and/or by stabilizers such as polyols (e.g. propylene glycol), boric acid, salts, sugar (e.g. glucose and sucrose) or sugar alcohols (e.g. sorbitol) or carbohydrates of low molecular weight. pH may be adjusted and stabilized, for instance with buffer salts such as salts from organic acids, e.g. sodium citrate and sodium lactate.

It has been found that α-galactosidase concentrate derivable from Aspergillus, in particular from *A. niger* or *A.*

*aculeatus* (having an enzyme activity of 250–100000 GALU/g, preferably an activity of 1000–25000 GALU/g, more preferably an activity of 2000–5000 GALU/g) is a very suitable enzyme concentrate.

1 GALU is the unit of α-galactosidase strength. It is defined as the amount of α-galactosidase required to form 1 μmole of p-nitro phenol+galactose from p-nitrophenyl α-D-galactopyranoside in one minute under standard conditions of pH 5.5 at 37° C. The procedure is further described below.

It has also been found that lactase concentrate (having an enzyme activity of 250–100000 LAU/g, preferably 1000–25000LAU/g, more preferably an activity of 2000–8000 LAU/g) is a very suitable enzyme concentrate.

1 LAU is the unit of lactase strength. It is defined as the amount of lactase required to release 1 μmole of glucose per minute from a solution of 4.75% w/v lactose in M-buffer pH 6.5 at 37° C. M-buffer is a special buffer designed to give the same major mineral concentrations as found naturally in cow's milk. M-buffer contains:

$Na_3$citrate X $2H_2O$: 2.70 mMoles/litre
5 Citric acid X $2H_2O$: 7.91 mMoles/litre
$K_2SO_4$: 1.03 mMoles/litre
$K_2HPO_4$: 2.99 mMoles/litre
$KH_2PO_4$: 10.80 mMoles/litre
KOH: 19.43 mMoles/litre
$MgCl_2 \times 6H_2O$: 4.08 mMoles/litre
$CaCl_2 \times 2H_2O$: 5.10 mMoles/litre
4N NaOH solution: 10.00 mMoles/litre
$NaHCO_3$: 3.33 mMoles/litre.

Granulation

In the process of the invention the powder may be made in accordance with well-known procedures of making wet granulation, for instance by using a convective mixer, preferably a high shear mixer, more preferably a high shear, high speed mixer, followed by fluid bed drying, optionally followed by a sieving. According to the invention it is preferred to use a high shear, high speed mixer of the trade mark "Fielder", "Lödige", "Diosna" or "Rowenta". High shear, high speed mixers from "Fielder", "Lödige" and "Diosna" are well known. A "Rowenta" consists of a sphere-shaped granulation chamber in which the carrier is mixed by means of a fast rotating knife, and the liquid enzyme preparation is poured into the unit from the top. The mixing is continued until the carrier is evenly wetted and a proper granulate has been formed. Accordingly, it will be understood that the term "powder" is also intended to include granulates. In accordance with this invention the directly compressible powder may contain no lubricants, or a lubricant may be added to the carbohydrate(s) before granulation (preferred), or a lubricant may be added during the granulation, or a lubricant may be added at a separate mixing after the granulation and before the tabletting. The lubricant may be added in an amount of at the most 20% (w/w), preferably in an amount of 0.25–10% (w/w).

According to the invention it is preferred to make a wet granulation consisting of a liquid enzyme preparation and a carrier, but the wet granulation may also consist of a carrier mixed with a spray-dried or freeze-dried enzyme powder whereto a liquid is added. The great disadvantage by using a spray-dried or freeze-dried enzyme powder is the dust problem described above.

In order to make a non-dusty powder the size of the particles is preferably at least 50 μm. On the other hand, they may also be too large to be directly compressible. It has been found that the particles of the powder may be in the range from 50–1500 μm, preferably in the range from 125–1000 μm, more preferably in the range from 150–700 μm.

It is important that the powder has the right water content in order to make it directly compressible. The water content is measured by loss on drying. A water content of at the most 10% (w/w), preferably a water content of 3–5% (w/w), may be accomplished by using any method known in the art, an example of which is conventional fluid-bed drying. The temperature of the fluid-bed should be adjusted to a level which does not deactivate the enzyme(s).

After fluid-bed drying the powder may be sieved, whereafter it is ready for tabletting.

Potential Applications

The directly compressible enzyme powder described in this invention may be used in all circumstances where a precise and safe dosage of an enzyme is needed or desired, for instance in dairies where a milk clotting enzyme may be added as tablets, or in the digestive aid industry for various digestive enzyme tablets, or in technical applications, for instance for washing, dish-washing and denim-washing purposes.

In particular for use as digestive aids, the tablets may be provided with an enteric coating to protect the enzyme(s) from degradation by gastric fluid. Examples of suitable enteric coating agents are cellulose acetate phthalate (CAP, Cellacephate®), vinyl acetate crotonic acid copolymer (Luviset®), methacrylic acid, (meth) acrylic acid ester copolymer (Eudragit®) or hydroxypropyl methylcellulose phthalate. For a further description of enteric coatings and coating processes, reference is made to WO 87/07292.

Manual Method For Determination of α-Galactosidase Activity

Reagents:

1. BUFFER: Acetate buffer 0.05M, DH 5.5

A: 11.55 ml of glacial acetic acid p.a. are dissolved in demineralized water. Make up to 1000 ml.

B: Dissolve 16.4 g of sodium acetate, p.a. in demineralized water and make up to 1000 ml.

Buffer: Mix 7.5 ml of A and 42.5 ml of B and make up to 200 ml with demineralized water.

Max. advisable storage time: 1 month at 25° C.

2. SUBSTRATE: 1.2 mM p-Nitrophenyl-α-D-galactopyranoside

Dissolve 0.0383 g of p-Nitrophenyl-α-D-galactopyranoside·1 $H_2O$ (Pierce N-0877) in acetate buffer 0.05M and make up to 100 ml.

Max. advisable storage time: 1 week at 4° C.

3. STOP REAGENT: Borax—NaOH buffer 0.0625M, pH 9.7

Dissolve 47.63 g of $Na_2B_4O_7 \cdot 10$ $H_2O$ in 500 ml of slightly heated demineralized water. Cool and transfer to a 2000 ml volumetric flask. Add demineralized water to approximate 1500 ml. Add 20 ml of 4N NaOH. Adjust pH to 9.7 with 4N NaOH and make up to the 200 ml mark with demineralized water.

Max. advisable storage time: 2 months at 25° C.

4. COLOUR STANDARD: 4-Nitrophenol. 240 μM

A: Dissolve 0.0334 g of 4-Nitrophenol (Merck 820896) in demineralized water. Make up to 1000 ml. 4 Nitrophenol should be handled in a well-ventilated room.

Make a standard curve as follows:

| | |
|---|---|
| I | 240 μM: A used undiluted |
| II | 160 μM: 100 ml of A + 50 ml of demineralized water |
| III | 80 μM: 50 ml of A + 100 ml of demineralized water |
| IV | 40 μM: 25 ml of A + 125 ml of demineralized water |

Max. advisable storage time: 1 month at 25° C.

Procedure:
Colour Standard

Make the colour standard values by mixing 2 ml of substrate and 1 ml of colour standard. Add 5 ml stop reagent.

When making the colour standard blank use demineralized water instead of colour standard. Measure $OD_{405}$.

Make standard and standard blank at room temperature.
Sample

Weigh and dilute the enzyme to a concentration corresponding to an activity of about 0.0015 GALU/ml.

|  | Sample | Sample blank |
| --- | --- | --- |
| Sample | 1 ml | 1 ml |
| Preheat substrate for 5 minutes | 37° C. |  |
| Add substrate (stop watch) and mix | 2 ml |  |
| Incubation for 15 minutes | 37° C. | room temp. |
| Add stop reagent and mix | 5 ml | 5 ml |
| Substrate - room temperature |  | 2 ml |
| Measure $OD_{405}$ within 30 minutes* |  |  |

*OD measurements should be finished within 30 minutes due to the risk of OD-change.

Calculation of Activity:

Make the colour standard curve ($\Delta$OD against concentration). The activity is calculated according to the following formula:

$$Act = \frac{(A_S - A_B) \cdot F_S \cdot 10^{-3}}{T \cdot M}$$

where $A_s$=The reading on the standard curve in $\mu$M 4-NP, corresponding to $OD_{405}$ for the sample.

$A_b$=The reading on the standard curve in $\mu$M 4-NP, corresponding to $OD_{405}$ for the sample blank.

$F_s$=Dilution factor for the sample.

T=Reaction time in minutes (=15).

M=Amount of sample weighed out.

$10^{-3}$=Conversion factor 1/ml.

The invention is further illustrated in the following examples which are not intended to be in any way limiting to the scope of the invention as claimed.

EXAMPLE 1

α-Galactosidase Powder(1)

α-Galactosidase Concentrate

α-galactosidase 1550 GALU/g

20% (w/w) sorbitol

2% (w/w) NaCl 10 3% (w/w) sodium citrate 0.2% (w/w) potassium sorbate pH of the α-galactosidase concentrate was 6.0. The portion of dry matter was approximately 50%.

Wet Granulation

A powder consisting of 45 g of a-galactosidase concentrate (see above)

133 g of maize starch (CERESTAR, GLOBE 03302)

43 g of sorbitol (ROQUETTE FRERES, NEOSORB 60)

was made in a Rowenta-mixer (MULTIMIXER KA-70). This powder was dried in a fluid-bed for 20 min. at 600° C. (the temperature of the product was max. 40° C).

The dried granulate was sieved through a sieve with a mesh size of 0.7 mm.

The dried and sieved granulate was tabletted without adding any other components. The tablets had a hardness of 11–12 kp. The disintegration time of the tablets was measured to approximately 5 min. in water at 37° C. (Ph. Eur.).

Tablet weight was 430 mg. The punches used were 10.5 mm (diameter), normal concave.

EXAMPLE 2

α-Galactosidase Powder (2)

a-Galactosidase Concentrate

The same as described in Example 1.

Wet Granulation

A powder consisting of 5 45 g of a-galactosidase concentrate (see Ex. 1)

125 g of maize starch (see Ex. 1)

60 g of sorbitol (see Ex. 1) was made in a Rowenta-mixer (see Ex. 1)

This powder was dried in a fluid-bed for 20 min. at 60° C. (the temperature of the product was max. 40° C.).

The dried granulate was sieved through a sieve with a mesh size of 0.7 mm.

1% Mg stearate was added to the dried and sieved granulate before tabletting. The resulting tablets had a hardness of 9–10 kp. The disintegration time of the tablets was measured to approximately 6 min. in water at 37° C. (Ph.Eur.). Tablet weight was 430 mg. The punches were 10.5 mm (diameter), normal concave.

EXAMPLE 3

α-Galactosidase Powder (3)

α-Galactosidase Concentrate

α-galactosidase 3000 GALU/g pH of the α-galactosidase-concentrate was 5.0. The portion of dry matter was approximately 48%.

Wet Granulation

A powder consisting of 45 g of α-galactosidase (described above)

133 g of maize starch (see ex.1)

43 g of sorbitol (see Ex. 1)

was made in a Rowenta-mixer (see Ex. 1).

This powder was dried in a fluid-bed for 20 min. at 60° C. (the temperature of the product was max. 40° C.).

The dried granulate was sieved through a sieve with a mesh size of 0.7 mm.

0.5% Mg stearate was added to the dried and sieved granulate before tabletting. The resulting tablets had a hardness of 3.5 kp. The disintegration time of the tablets was measured to <10 min. in water at 37° C (Ph.Eur.). Tablet weight was 251 mg. The punches used were 8.0 mm (diameter), normal concave.

EXAMPLE 4

α-Galactosidase Powder (4)

α-Galactosidase Concentrate

α-Galactosidase 3930 GALU/g pH of the concentrate was 5.0. The dry matter content approximately 48%.

Wet Granulation

A powder consisting of 24.7 g of α-Galactosidase (described above)

126.0 g of maize starch (see Ex. 1)

50.0 g of sucrose powder (DDS, Flor)

20 10.0 g of hydrogenated vegetable oil (Edward Mendell, Lubritab)

was made in a Rowenta-mixer (see Ex. 1).

The powder was dried in a fluid-bed for 20 min. at 60° C. (the temperature of the product was max. 40° C.). The dried granulate was sieved through a sieve with a mesh size of 0.7 mm.

The sieved granulate was compressed into tablets in an excenter tabletting Machine. The resulting tablets had a hardness of approx. 6 kp and the disintegration time was measured to less then 10 min. in water at 37° C. (Ph.Eur.). Tablet weight was 333 mg. The punches used were 9.5 mm (diameter), normal concave.

EXAMPLE 5

α-Galactosidase Powder (5)

α-Galactosidase Concentrate

α-Galactosidase 3930 GALU/g pH of the concentrate was 5.0. The dry matter content approximately 48%.

Wet Granulation

A powder consisting of
24.7 g of α-Galactosidase (described above)
126.0 g of maize starch (see Ex. 1)
50.0 g of sorbitol (see Ex. 1)
10.0 g of hydrogenated vegetable oil (Edward Mendell, Lubritab)

was made in a Rowenta-mixer (see Ex. 1)

The powder was dried in a fluid-bed for 20 min. at 60° C. (the temperature of the product was max. 40° C.). The dried granulate was sieved through a sieve with a mesh size of 0.7 mm.

The sieved granulate was compressed into tablets in an excenter tabletting machine. The resulting tablets had a hardness of approx. 6 kp, and the disintegration time was measured to less than 10 min. in water at 37° C. (Ph.Eur.). Tablet weight was 333 mg. The punches used were 9.5 mm (diameter), normal concave.

EXAMPLE 6

α-Galactosidase Powder (6)

α-Galactosidase Concentrate

α-Galactosidase 3930 GALU/g pH of the concentrate was 5.0. The dry matter content approximately 48%.

Wet Granulation

A powder consisting of
24.7 g of α-Galactosidase (described above)
126.0 g of maize starch (see Ex. 1)
50.0 g of mannitol (Roquette Freres, Standard)
10.0 g of hydrogenated vegetable oil (Edward Mendell, Lubritab)

was made in a Rowenta-mixer (see Ex. 1).

The powder was dried in a fluid-bed for 20 min. at 60° C. (the temperature of the product was max. 40° C.). The dried granulate was sieved through a sieve with a mesh size of 0.7 mm.

The sieved granulate was compressed into tablets in an excenter tabletting machine. The resulting tablets had a hardness of approx. 2 kp, and the disintegration time was measured to less than 10 min. in water at 37° C. (Ph.Eur.). Tablet weight was 333 mg. The punches used were 9.5 mm (diameter), normal concave.

EXAMPLE 7

α-Galactosidase Powder (7)

α-Galactosidase Concentrate

α-Galactosidase 3930 GALU/kg pH of the concentrate was 5.0. The dry matter content approximately 48%.

Wet Granulation

A powder consisting of
24.7 g of α-Galactosidase (described above)
108.0 g of maize starch (see Ex. 1)
25.0 g of mannitol (see Ex. 6)
43.0 g of sorbitol (see Ex. 1)
10.0 g of hydrogenated vegetable oil (Edward Mendell, Lubritab)

was made in a Rowenta-mixer (see Ex. 1).

The powder was dried in a fluid-bed for 20 min. at 60° C. (the temperature of the product was max 40° C.). The dried granulate was sieved through a sieve with a mesh size of 0.7 mm.

The sieved granulate was compressed into tablets in an excenter tabletting machine. The resulting tablets had a hardness of approx. 5 kp, and the disintegration time was measured to less than 10 min. in water at 37° C. (Ph.Eur.). Tablet weight was 333 mg. The punches used were 9.5 mm (diameter), normal concave.

EXAMPLE 8

Lactase Powder (1)

Lactase Concentrate
Lactase 6400 LAU/g
32% (w/w) sorbitol
0.2% (w/w) Potassium sorbate pH of the concentrate was 5.4. The portion of dry matter was approximately 50%.

Wet Granulation

A powder consisting of
50.0 g of Lactase Concentrate (described above)
126.0 g maize starch (see Ex. 1)
50.0 g of sucrose powder (see Ex. 4)
10.0 g of hydrogenated vegetable oil (Edward Mendell, Lubritab)

was made in a Rowenta-mixer (see Ex. 1).

The powder was dried in a fluid-bed for 20 min. at 60° C. (the temperature of the product was max. 40° C.). The dried granulate was sieved through a sieve with a mesh size of 0.7 mm.

The sieved granulate was compressed into tablets in an excenter tabletting machine. The resulting tablets had a hardness of approx. 6–8 kp, and the disintegration time was measured to less than 10 min. in water at 37° C. (Ph.Eur.). Tablet weight was 333 mg. The punches used were 9.5 mm (diameter), normal concave.

EXAMPLE 9

Lactase Powder (2)

Lactase Concentrate
Lactase 4500 LAU/g

The dry matter was approximately 52%.

Wet Granulation

A powder consisting of
50.0 g of Lactase Concentrate (described above)
126.0 g of maize starch (see Ex. 1)
50.0 g of sucrose powder (see Ex. 4)
10.0 g of hydrogenated vegetable oil (Edward Mendell, Lubritab)

was made in a Rowenta-mixer (see Ex. 1)

The powder was dried in a fluid-bed for 20 min. at 60° C. (the temperature of the product was max. 40° C.). The dried granulate was sieved through a sieve with a mesh size of 0.7 mm.

The sieved granulate was compressed into tablets in an excenter tabletting machine. The resulting tablets had a hardness of approx. 6–8 kp, and the disintegration time was measured to less than 10 min. in water at 37° C. (Ph.Eur.). Tablet weight was 400 mg. The punches used were 9.5 mm (diameter), normal concave.

What is claimed is:

1. A process or preparing an enzyme-containing tablet comprising mixing a liquid enzyme preparation with one or more carbohydrate(s), subjecting the resulting mixture to drying and sieving so as to obtain a powder having a particle size in the range from 50 to 1500 μm and subjecting the resulting powder directly to tabletting.

2. The process according to claim 1, wherein the powder has a particle size in the range from 125 to 1000 μm.

3. The process according to claim 1, wherein the powder has a particle size in the range from 150 to 700 μm.

4. The process according to claim 1, wherein a lubricant in an amount of at the most 20% (w/w) is added to the carbohydrate(s) before mixing with the liquid enzyme preparation.

5. The process according to claim 1, wherein a lubricant in an amount of 0.25–10% (w/w) is added to the carbohydrate(s) before mixing with the liquid enzyme preparation.

6. The process according to claim 1, wherein a lubricant in an amount of at the most 20% (w/w) is added during mixing.

7. The process according to claim 1, wherein a lubricant in an amount of 0.25–10% (w/w) is added during mixing.

8. The process according to claim 1, wherein a lubricant in an amount of at the most 20% (w/w) is added after mixing, drying and sieving.

9. The process according to claim 1, wherein a lubricant in an amount of 0.25–10% (w/w), is added after mixing, drying and sieving.

10. The process according to claim 1, wherein the liquid enzyme preparation is mixed with one or more carbohydrates in convective manner.

11. The process according to claim 1, wherein the convective manner is a high shear mixer.

12. The process according to claim 1, wherein the convective mixer is a high shear, high speed mixer.

13. The process according to claim 1, wherein the carbohydrate is a starch, a sugar, a sugar alcohol, a mixture of a sugar and a sugar alcohol, or a mixture of a starch and a sugar and/or a sugar alcohol.

14. The process according to claim 1, wherein the carbohydrate is a starch of vegetable origin.

15. The process according to claim 1, wherein the carbohydrate is maize starch, potato starch, rice starch or wheat starch.

16. The process according to claim 1, wherein the starch is maize starch.

17. The process according to claim 1, wherein the carbohydrate is a mono-, di- or oligosaccharide.

18. The process according to claim 1, wherein the carbohydrate is an alcohol of a mono-, di- or trisaccharide.

19. The process according to claim 1, wherein the carbohydrate is sucrose, maltose, lactose, galactose, fructose or glucose.

20. The process according to claim 1, wherein the carbohydrate is sorbitol, mannitol or xylitol.

21. The process according to claim 1, wherein the carbohydrate is sorbitol.

22. The process according to claim 1, wherein the carbohydrate is a mixture of 65–90% (w/w) maize starch and 10–35% (w/w) sorbitol.

23. The process according to claim 1, wherein the enzyme is a microbial enzyme or an enzyme of animal or plant origin.

24. The process according to claim 1, wherein the enzyme is a mixture of two or more enzymes.

25. The process according to claim 1, wherein the enzyme is an enzyme useful for the preparation of food and feed, a medical enzyme, an enzyme useful for digestive aids or an enzyme useful for technical applications.

26. The process according to claim 1, wherein the enzyme is an oxidoreductase, a hydrolase, an isomerase or any mixture thereof.

27. The process according to claim 1, wherein the enzyme is a α-galactosidase.

28. The process according to claim 1, wherein the enzyme is a α-galactosidase derived from Aspergillus.

29. The process according to claim 1, wherein the enzyme is a α-galactosidase derived from *A. niger* or *A. aculeatus*.

30. The process according to claim 1, wherein the enzyme is a liquid α-galactosidase preparation having an activity of 250–100000 GALU/g.

31. The process according to claim 1, wherein the enzyme is a liquid α-galactosidase preparation having an activity of 1000–25000 GALU/g.

32. The process according to claim 1, wherein the enzyme is a liquid α-galactosidase preparation having an activity of 2000–5000 GALU/g.

33. The process according to claim 1, wherein the carbohydrate is a mixture of maize starch and sorbitol and the enzyme is a liquid α-galactosidase preparation.

34. A directly compressible powder, which consists essentially of a carbohydrate and an enzyme.

35. The powder according to claim 34, wherein the powder is free flowing.

36. The powder according to claim 34, wherein the powder has a particle size in the range from 125 to 1000 μm.

37. The powder according to claim 34, wherein the powder has a particle size in the range from 150 to 700 μm.

38. The powder according to claim 34, wherein the powder has a water content of at most 10% (w/w), measured by loss on drying.

39. The powder according to claim 34, wherein the powder has a water content in the range of 3–5% (w/w), measured by loss on drying.

40. The powder according to claim 34, wherein the carbohydrate is a starch, a sugar, a sugar alcohol, a mixture of a sugar and a sugar alcohol, or a mixture of a starch and a sugar alcohol.

41. The powder according to claim 34, wherein the carbohydrate is a starch of vegetable origin.

42. The powder according to claim 34, wherein the carbohydrate is maize starch, potato starch, rice starch or wheat starch.

43. The powder according to claim 34, wherein the starch is maize starch.

44. The powder according to claim 34, wherein the carbohydrate is a mono-, di-, or oligosaccharide.

45. The powder according to claim 34, wherein the carbohydrate is an alcohol of a mono-, di-, or trisaccharide.

46. The powder according to claim 34, wherein the carbohydrate is sucrose, maltose, lactose, galactose, fructose, or glucose.

47. The powder according to claim 34, wherein the carbohydrate is sorbitol, mannitol, or xylitol.

48. The powder according to claim 34, wherein the carbohydrate is sorbitol.

49. The powder according to claim 34, wherein the carbohydrate is a mixture of 65–90% (w/w) maize starch and 10–35% (w/w) sorbitol.

50. The powder according to claim 34, wherein the enzyme is a microbial enzyme or an enzyme of animal or plant origin.

51. The powder according to claim 34, wherein the enzyme is a mixture of two or more enzymes.

52. The powder according to claim 34, wherein the enzyme is an enzyme useful for the preparation of food and feed, a medical enzyme, an enzyme useful for digestive aids or an enzyme useful for technical applications.

53. The powder according to claim 34, wherein the enzyme is an oxidoreductase, a hydrolase, an isomerase or any mixture thereof.

54. The powder according to claim 34, wherein the enzyme is a α-galactosidase.

55. The powder according to claim 34, wherein the enzyme is a α-galactosidase derived from Aspergillus.

56. The powder according to claim 34, wherein the enzyme is a α-galactosidase derived from *A. niger* or *A. aculeatus*.

57. The powder according to claim 34, wherein the enzyme is a liquid α-galactosidase preparation having an activity of 250–100000 GALU/g.

58. The powder according to claim 34, wherein the enzyme is a liquid α-galactosidase preparation having an activity of 1000–25000 GALU/g.

59. The powder according to claim 34, wherein the enzyme is a liquid α-galactosidase preparation having an activity of 2000–5000 GALU/g.

60. The powder according to claim 34, wherein the carbohydrate is a mixture of maize starch and sorbitol and the enzyme is a liquid α-galactosidase preparation.

* * * * *

UNITED STATES PATENT AND TRADEMARK OFFICE
CERTIFICATE OF CORRECTION

PATENT NO. : 5,885,618

DATED : March 23, 1999

INVENTOR(S) : Knap et al.

It is certified that error appears in the above-identified patent and that said Letters Patent is hereby corrected as shown below:

Col. 9, line 66, claim 25    delete "medical" and insert --medicinal--

Col. 11, line 1, claim 52    delete "medical" and insert --medicinal--

Signed and Sealed this

Fifteenth Day of February, 2000

Q. TODD DICKINSON

*Attest:*

*Attesting Officer*        *Commissioner of Patents and Trademarks*